US009125630B2

(12) United States Patent
Menzel

(10) Patent No.: US 9,125,630 B2
(45) Date of Patent: Sep. 8, 2015

(54) DYNAMICALLY RECONFIGURING A USER INTERFACE OF A PATIENT MONITOR RESPONSIVE TO AN ORIENTATION INPUT

(75) Inventor: Frank Menzel, Oakland, NJ (US)

(73) Assignee: SHENZHEN MINDRAY BIO-MEDICAL ELECTRONICS CO. LTD., Shenzhen (CN)

( * ) Notice: Subject to any disclaimer, the term of this patent is extended or adjusted under 35 U.S.C. 154(b) by 985 days.

(21) Appl. No.: 13/284,324

(22) Filed: Oct. 28, 2011

(65) Prior Publication Data

US 2013/0109928 A1   May 2, 2013

(51) Int. Cl.
| | |
|---|---|
| A61B 5/00 | (2006.01) |
| G06F 3/06 | (2006.01) |
| G06F 19/00 | (2011.01) |
| G06F 3/00 | (2006.01) |
| A61B 5/01 | (2006.01) |
| A61B 5/021 | (2006.01) |
| A61B 5/024 | (2006.01) |
| A61B 5/0402 | (2006.01) |
| A61B 5/08 | (2006.01) |
| A61B 5/145 | (2006.01) |

(52) U.S. Cl.
CPC ............ *A61B 5/7445* (2013.01); *G06F 3/0601* (2013.01); *G06F 19/3406* (2013.01); *A61B 5/01* (2013.01); *A61B 5/021* (2013.01); *A61B 5/024* (2013.01); *A61B 5/0402* (2013.01); *A61B 5/08* (2013.01); *A61B 5/14542* (2013.01)

(58) Field of Classification Search
CPC .............................. A61B 5/0002; G06F 19/32
See application file for complete search history.

(56) References Cited

U.S. PATENT DOCUMENTS

| | | | | |
|---|---|---|---|---|
| 7,978,176 | B2 * | 7/2011 | Forstall et al. | 345/158 |
| 8,325,151 | B1 * | 12/2012 | Chan et al. | 345/173 |
| 2008/0177160 | A1 * | 7/2008 | Al Ali et al. | 600/309 |
| 2009/0172531 | A1 * | 7/2009 | Chen et al. | 715/702 |
| 2010/0100623 | A1 * | 4/2010 | Wulff et al. | 709/224 |
| 2011/0029865 | A1 * | 2/2011 | Gilland et al. | 715/702 |
| 2012/0084734 | A1 * | 4/2012 | Wilairat | 715/863 |

OTHER PUBLICATIONS

Clifford, M. et al; "Measuring Tilt with low-g accelerometers"; Freescale Semiconductors, AN 3107, 2005, pp. 1-8.*

* cited by examiner

*Primary Examiner* — William Thomson
*Assistant Examiner* — Marie Archer
(74) *Attorney, Agent, or Firm* — Kory D. Christensen; Stoel Rives LLP

(57) ABSTRACT

A patient monitoring system may be configured to acquire data signals relating to various physiological parameters of a patient. For example, the patient monitoring system may be used to determine or record a patient's blood pressure, heart rate, temperature, and/or other physiological parameters. The patient monitoring system may process the data signals and generate patient parameter information. The patient parameter information may be displayed on a display unit. The patient monitoring system may be configured to dynamically reconfigure a visual display of the patient parameter information based on the orientation (e.g., portrait or landscape) of the patient monitoring system. Additionally, the patient monitoring system may be configured to selectively enter a transport mode, in which the touch screen and/or user inputs are locked or partially locked. The patient monitoring system may automatically enter a transport mode when the display unit is rotated to a landscape orientation.

34 Claims, 14 Drawing Sheets

DYNAMICALLY RECONFIGURING A USER INTERFACE OF A PATIENT MONITOR RESPONSIVE TO AN ORIENTATION INPUT

TECHNICAL FIELD

This disclosure relates to patient monitors. Specifically, this disclosure relates to patient monitoring systems configured to dynamically reconfigure a visual layout of a user interface as a display unit is rotated between portrait and landscape orientations.

SUMMARY

According to various embodiments, a patient monitoring system is configured to acquire data signals relating to various physiological parameters of a patient. For example, the patient monitoring system may be used to determine or record a patient's blood pressure, heart rate, temperature, and/or other physiological parameters. The patient monitoring system may process the data signals and generate patient parameter information. The patient parameter information may be displayed on a display unit for use by a medical practitioner or other user. The display unit may be a touch screen display and/or include other inputs, such as buttons or switches. The patient monitoring system may be configured to selectively enter a transport mode, in which the touch screen and/or user inputs are disabled or partially disabled. In some embodiments, a patient monitoring system automatically enters a transport mode when the display unit is rotated to a landscape orientation. Alternatively, an operator may provide manual input causing the display unit to enter a transport mode. Additional aspects will be apparent from the following detailed description, which proceeds with reference to the accompanying drawings.

DETAILED DESCRIPTION

Figure 1:
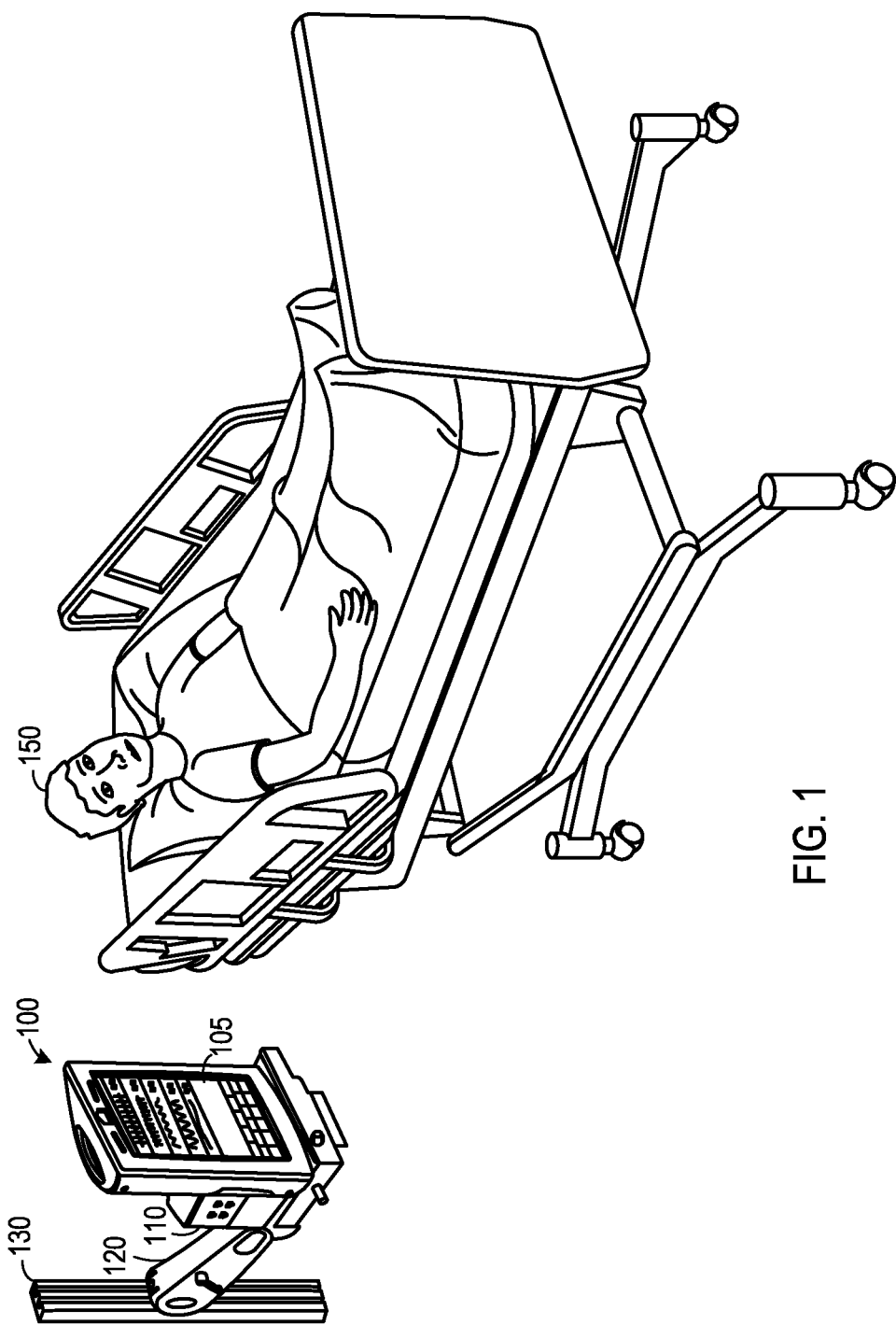
FIG. 1 is a perspective view of a wall-mounted patient monitoring system in a portrait orientation near a patient.

Patient monitoring systems may be used to acquire data signals relating to physiological parameters of a patient, analyze the data signals, and display patient parameter information on a display unit. Sensors and probes attached to the patient may facilitate the collection of data relating to physiological parameters such as, for example, pulse rate, temperature, respiration rate, blood pressure, blood oxygen, electrocardiogram, etc.

According to various embodiments, a patient monitoring system may selectively display a visual layout of the patient parameter information in a portrait orientation. The patient monitoring system may be removed from a mount and placed beside a patient in a landscape orientation while the patient is transported. The patient monitoring system may continually monitor the patient during transport. During transport, the patient monitoring system may display a visual layout of the patient parameter information in a landscape orientation. The visual layout in the landscape orientation may prominently display the information most pertinent during the transportation of the patient and/or remove or minimize some menu options. Additionally, the display unit may enter a transport mode, locking or partially locking a touch screen display to reduce or eliminate accidental inputs.

In one embodiment, a patient monitoring system includes a parameter acquisition unit, a processing unit, an orientation unit, a layout unit, and a display interface unit. The parameter acquisition unit may be configured to acquire the data signals relating to the physiological parameters of the patient. The processing unit may generate patient parameter information based on the data signals. An orientation unit may receive an orientation input corresponding to the orientation of a display unit. For example, the orientation unit may be in communication with an accelerometer configured to indicate whether the display unit is in a portrait orientation or a landscape orientation. Alternatively, the display unit may be configured to receive manual input from an operator indicating whether the display unit is in a portrait orientation or a landscape orientation.

The layout unit may then configure an appropriate visual layout of a user interface for display on the display unit based on the current orientation. According to various embodiments, the visual layout includes at least a portion of the patient parameter information and/or the acquired data signals. For example, the layout unit may prepare a visual layout in a portrait orientation based on an input indicating that the display unit is in a portrait orientation. The layout unit may dynamically reconfigure a visual layout based on an input indicating that the display unit has transitioned to a landscape orientation.

According to various embodiments, the layout unit may be configured to dynamically reconfigure the visual layout of the user interface and patient parameter information based on any number of possible orientations. For example, in addition to landscape and portrait orientations, the orientation unit may be configured to receive an input indicating that the display unit is in any possible permutation of portrait and landscape orientations in which a display unit is face-up, face-down, right-facing, left-facing, front-facing, or rear-facing. Accordingly, the layout unit may dynamically reconfigure the visual layout of the patient parameter information for any possible orientation.

A display interface unit may be configured to display the visual layout prepared by the visual layout unit. Additionally, the display interface unit may be configured to receive operator inputs from a touch screen and/or from buttons or switches on the front of the display unit.

According to some embodiments, the display unit is configured to enter a transport mode when the orientation unit receives an orientation input indicating that the display unit is in the landscape orientation. For example, when a display unit is placed in a landscape orientation an accelerometer or similar device may automatically detect the orientation and the display unit may enter the transport mode. Alternatively, an operator may provide an input indicating that the display unit is in a landscape orientation causing the display unit to enter the transport mode. According to another alternative, an operator may selectively cause the display unit to enter the transport mode independent of the orientation of the display unit. Additionally, an operator may selectively exit the transport mode by rotating the display unit to a portrait orientation or by providing an appropriate manual input.

According to various embodiments, when the display unit enters the transport mode it may lock a touch screen display, such that the touch screen display does not register touch inputs. Alternatively, the touch screen display may be partially locked, such that the touch screen only registers touch inputs that are held for an extended period of time or touch inputs in a particular area of the touch screen display.

Some of the infrastructure that can be used with embodiments disclosed herein is already available, such as: general-purpose computers, computer programming tools and techniques, digital storage media, and communications networks. A computer may include a processor such as a microprocessor, microcontroller, logic circuitry, or the like. The processor may include a special purpose processing device such as an ASIC, PAL, PLA, PLD, FPGA, or other customized or programmable device. The computer may also include a computer-readable storage device such as non-volatile memory, static RAM, dynamic RAM, ROM, CD-ROM, disk, tape, magnetic, optical, flash memory, or other computer-readable storage medium.

Various aspects of certain embodiments may be implemented using hardware, software, firmware, and/or a combination thereof. As used herein, a software module or component may include any type of computer instruction or computer executable code located within or on a computer-readable storage medium. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a computer-readable storage medium, which together implement the described functionality of the module. Indeed, a module may comprise a single instruction or many instructions, and may be distributed over several different code segments, among different programs, and across several computer-readable storage media. Some embodiments may be practiced in a distributed computing environment where tasks are performed by a remote processing device linked through a communications network.

The embodiments of the disclosure will be best understood by reference to the drawings, wherein like parts are designated by like numerals throughout. The components of the disclosed embodiments, as generally described and illustrated in the figures herein, could be arranged and designed in a wide variety of different configurations. Furthermore, the described features, structures, or operations may be combined in any suitable manner in one or more embodiments. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor need the steps be executed only once.

FIG. 1 is a perspective view of a wall-mounted patient monitoring system 100 in a portrait orientation near a patient 150. As illustrated, the patient monitoring system 100 may include various communication ports 110 and may be mounted to a wall. A mounting arm 120 and a wall plate 130 may allow the patient monitoring system 100 to be pivoted and vertically adjusted. The patient monitoring system 100 may be any shape, size, and/or dimension.

The communication ports 110 may include any of a wide variety of port types and sizes. For example, the communication ports 110 may include network ports, such as RJ-45 Ethernet ports and RS-232 ports, nurse call ports, coaxial ports, and/or specialized ports for connecting physiological sensor probes, such as $SpO_2$ ports. The communication ports 110 may be utilized to connect various physiological sensors (not shown) to the patient monitoring system 100. The various physiological sensors may be used to acquire data signals related to physiological parameters of the patient 150.

For example, the communication ports 110 may be used to acquire data signals relating to pulse rate, temperature, respiration rate, blood pressure, venous oxygen saturation, electrocardiogram information, and the like. The patient monitoring system 100 may be configured to process the data signals in order to generate patient parameter information relating to the physiological parameters of the patient 150. Additionally, the patient monitoring system 100 may be configured to upload, store, and/or display the patient parameter information via a display unit 105.

The display unit 105 of the patient monitoring system 100 may include an integrated touch screen configured to receive operator inputs. Alternatively or additionally, the patient monitoring system 100 may include one or more peripheral devices, such as a keyboard or mouse. The display unit 105 may have a vertical dimension larger than a horizontal dimension, i.e. it may be in a portrait orientation. In certain embodiments, orienting display unit 105 in a portrait orientation allows for a larger number of vertically aligned rectangular regions, and thus a larger number of patient parameter waveforms, to be displayed than if display unit 105 were oriented in a landscape orientation. Particularly, as orienting display unit 105 in a portrait orientation allows for an increased vertical dimension, more vertically aligned waveforms may be displayed on the interface. While orienting display unit 105 in a portrait orientation may reduce the length of the horizontally displayed time parameters of the patient parameter waveforms, the added benefit of displaying a greater number of patient parameter waveforms may be of increased importance to a clinical practitioner.

Figure 2:
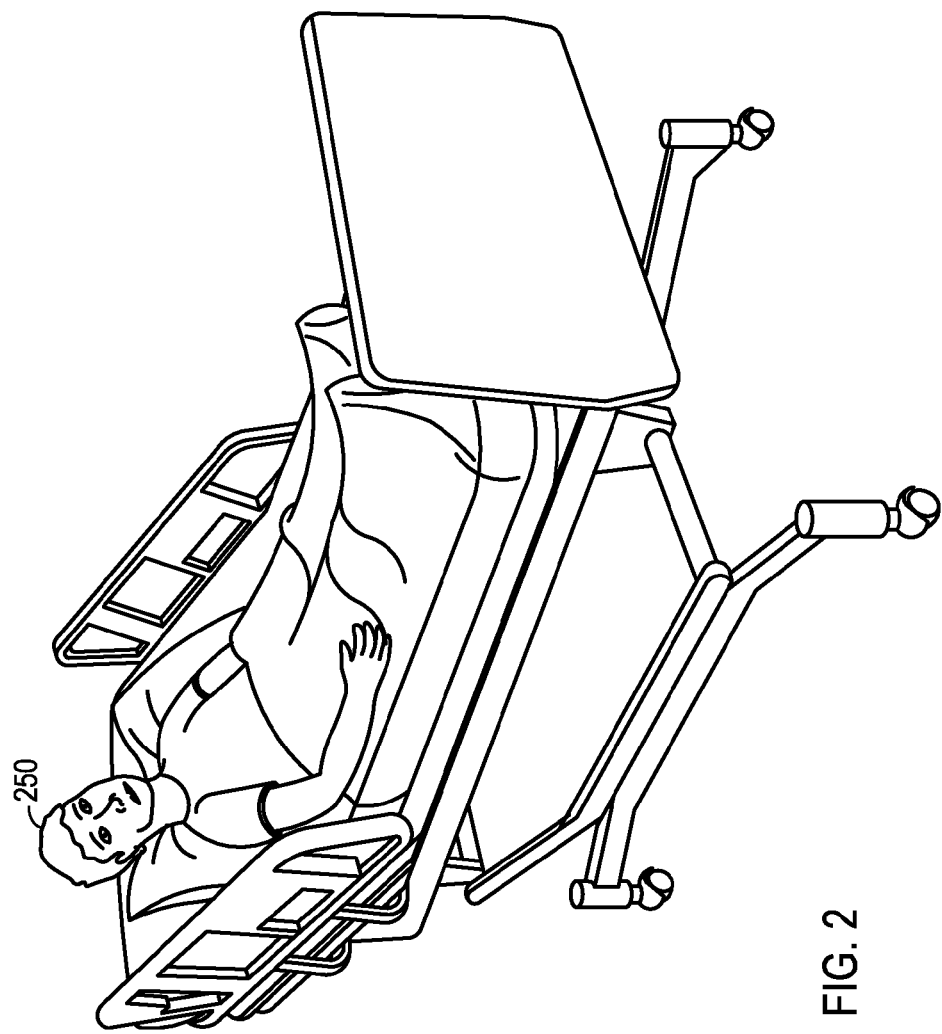
FIG. 2 is a perspective view of a wall-mounted patient monitoring system in a landscape orientation near a patient.
Figure 2:
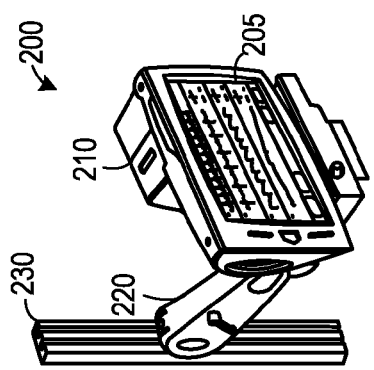

FIG. 2 is a perspective view of a wall-mounted patient monitoring system 200 in a landscape orientation beside a patient 250. Again, a mounting arm 220 and a wall plate 230 may allow the patient monitoring system 200 to be pivoted and vertically adjusted. Additional communications ports 210 may provide for additional data signals related to the patient and/or network connectivity.

The display unit 205 of the patient monitoring system 200 may include an integrated touch screen allowing for operator input. As illustrated, the display unit 205 may be rotated from the portrait orientation (illustrated in FIG. 1) to a landscape orientation. According to various embodiments, the patient monitoring system is configured to automatically detect that the display unit 205 is in the landscape orientation and present an appropriate visual layout of the patient parameter information in a landscape orientation. While the portrait orientation may generally be preferable in some contexts, the ability to rotate the display unit 205 to a landscape orientation may provide increased flexibility. Additionally, as discussed below in greater detail, a landscape orientation may provide for increased stability during transport of patient 250.

Figure 3:
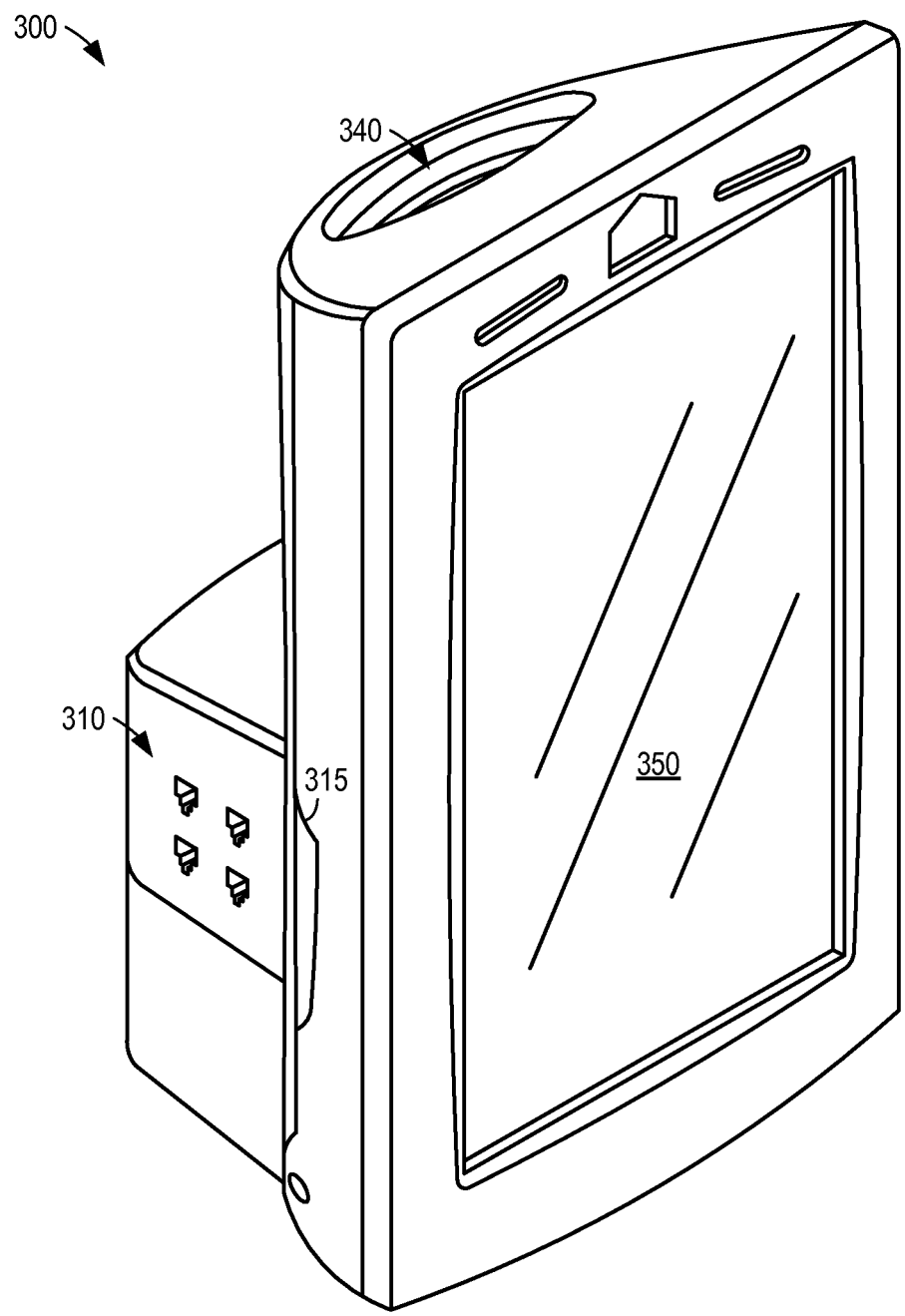
FIG. 3 is a perspective view of a patient monitoring system in a portrait orientation, including various communication ports.

FIG. 3 is a perspective view of a patient monitoring system 300 in a portrait orientation, including various communication ports 310. Any number of ports and types of ports may be utilized. For example, the communication ports 310 may include network ports, nurse call ports, coaxial ports, and/or specialized ports for connecting physiological sensor probes, such as $SpO_2$ ports. Data signals acquired via the communication ports 310 may be processed to generate patient parameter information. The data signals and/or the patient parameter information may be displayed on the display unit 350. As illustrated, a handle 340 may provide a grip for the movement, transportation, and rotation of the patient monitoring system 300. Grips 315 on each side of the patient monitoring system 300 may also facilitate the movement, transportation, and/or rotation of the patient monitoring system 300. Additionally, the grips 315 may be used to remove patient monitoring system 300 from a mount or stand. For example, the grips 315 may include releases that may be actuated by an operator in order to remove the patient monitoring system 300 from a wall mount.

The display unit 350 of the patient monitoring system 300 may include an integrated touch screen. The portrait orientation of display unit 350 allows for an increased number of vertically aligned patient parameter waveforms to be displayed. In certain embodiments, display unit 350 may have omni-directional visibility and be capable of being viewed from a wide variety of angles. In some embodiments, backlight inverters (not shown) included in display unit 350 may be oriented in a manner allowing for operation in both portrait and landscape orientations. In other embodiments, display unit 350 may be lit using light-emitting diodes (LEDs).

The embodiments of the patient monitoring systems 100, 200, and 300 shown in FIGS. 1-3 are provided by way of example, and a skilled artisan will understand from the disclosure that any patient monitoring system may be used with the embodiments disclosed herein.

Figure 4A:
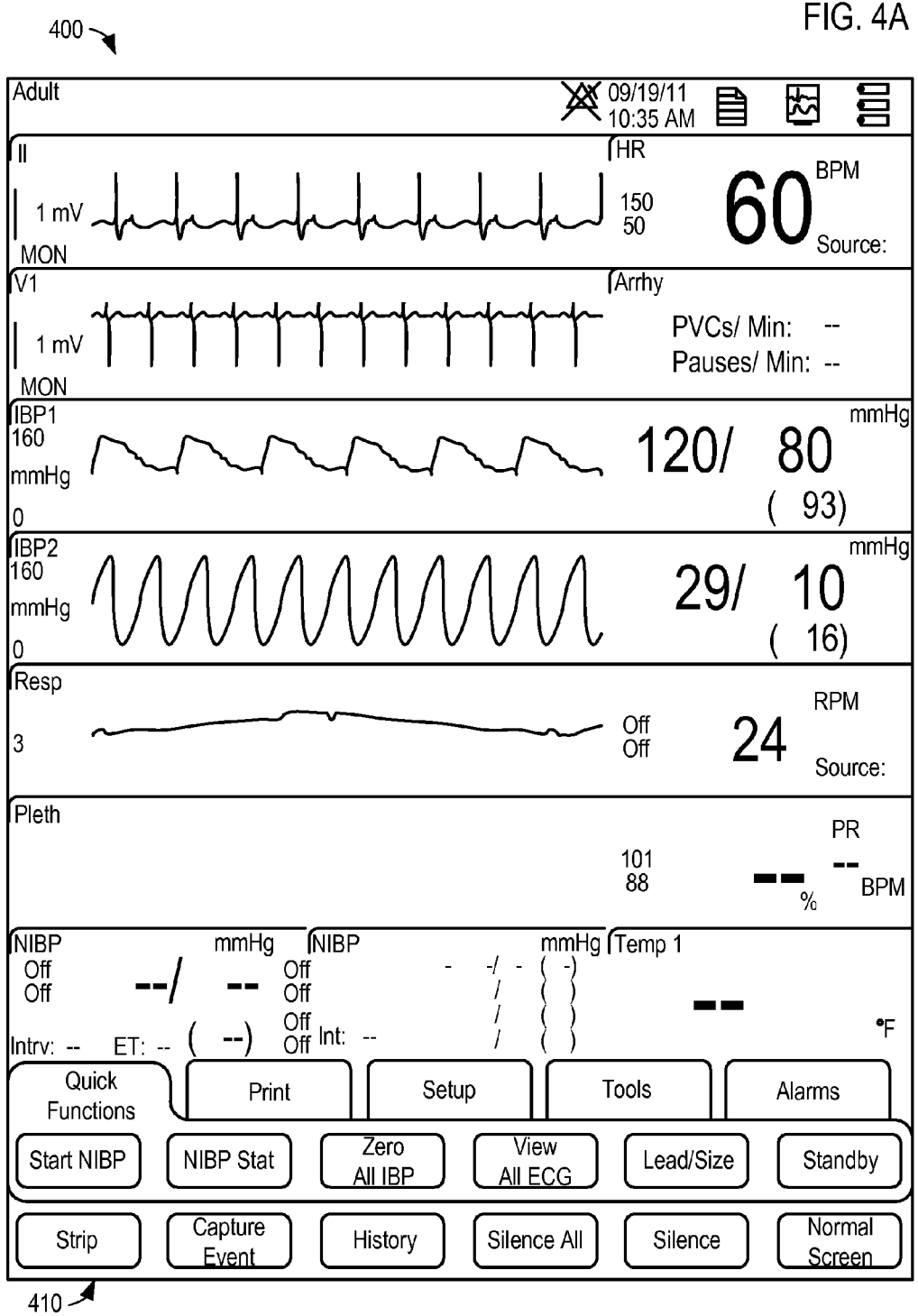
FIG. 4A is an exemplary screenshot of a touch screen display unit of a patient monitoring system in a portrait orientation, including various menu tabs.

FIG. 4A is an exemplary screenshot of a touch screen interface 400 of a display unit of a patient monitoring system in a portrait orientation, including various menu tabs 410. The touch screen interface 400 may display waveforms and/or numerical values corresponding to acquired data signals and/or processed patient parameter information. As illustrated, various menu tabs 410 may allow an operator to enter information, retrieve additional information, modify the display format, add or remove waveforms and/or numerical values, and/or modify how information is displayed. The menu tabs, buttons, and icons 410 are exemplified by rounded rectangular regions; however, any possible shape, size, or configuration may be utilized in practice.

As illustrated, a touch screen interface may include one or more user-selectable interface buttons, such as a function menu button, a print menu button, a setup menu button, a tools menu button, a procedures menu button, an alarms menu button, and the like. In certain embodiments, when one of the user-selected interface buttons is selected, a further set of user-selectable interface buttons (e.g., a sub-menu) may be displayed.

With the touch screen interface 400 in a portrait orientation, a plurality of vertically aligned rectangular regions may be positioned above the menu tabs section 410. Each of the rectangular regions may be user-selectable and allow an operator to modify how patient parameter information is displayed, add information, and/or delete information. While a portrait orientation may reduce the length of the horizontally displayed time parameters of the patient parameter waveforms, the added benefit of displaying a greater number of patient parameter waveforms may be of increased importance to a clinical practitioner. Exemplary waveforms and corresponding numerical values are illustrated in FIG. 4A. However, it will be apparent to one having skill in the art that any monitored physiological condition of a patient may be displayed as a waveform and/or numerical value.

A display unit may be configured with an accelerometer or similar device configured to automatically detect when the display unit is rotated between the portrait orientation and the landscape orientation. Such a patient monitoring system may dynamically reconfigure a visual layout of the touch screen interface 400 when the display unit is rotated between portrait and landscape orientations. For example, if the display unit is rotated to a landscape orientation, the visual layout of the touch screen interface 400 may be dynamically reconfigured for display in a landscape orientation. Similarly, if the display unit is rotated to a portrait orientation, then the visual layout of the touch screen interface 400 may be dynamically reconfigured for display in a landscape orientation. Alternatively or additionally, an operator may select an icon, actuate a switch, and/or push a button to manually display a visual layout for a landscape orientation.

Figure 4B:
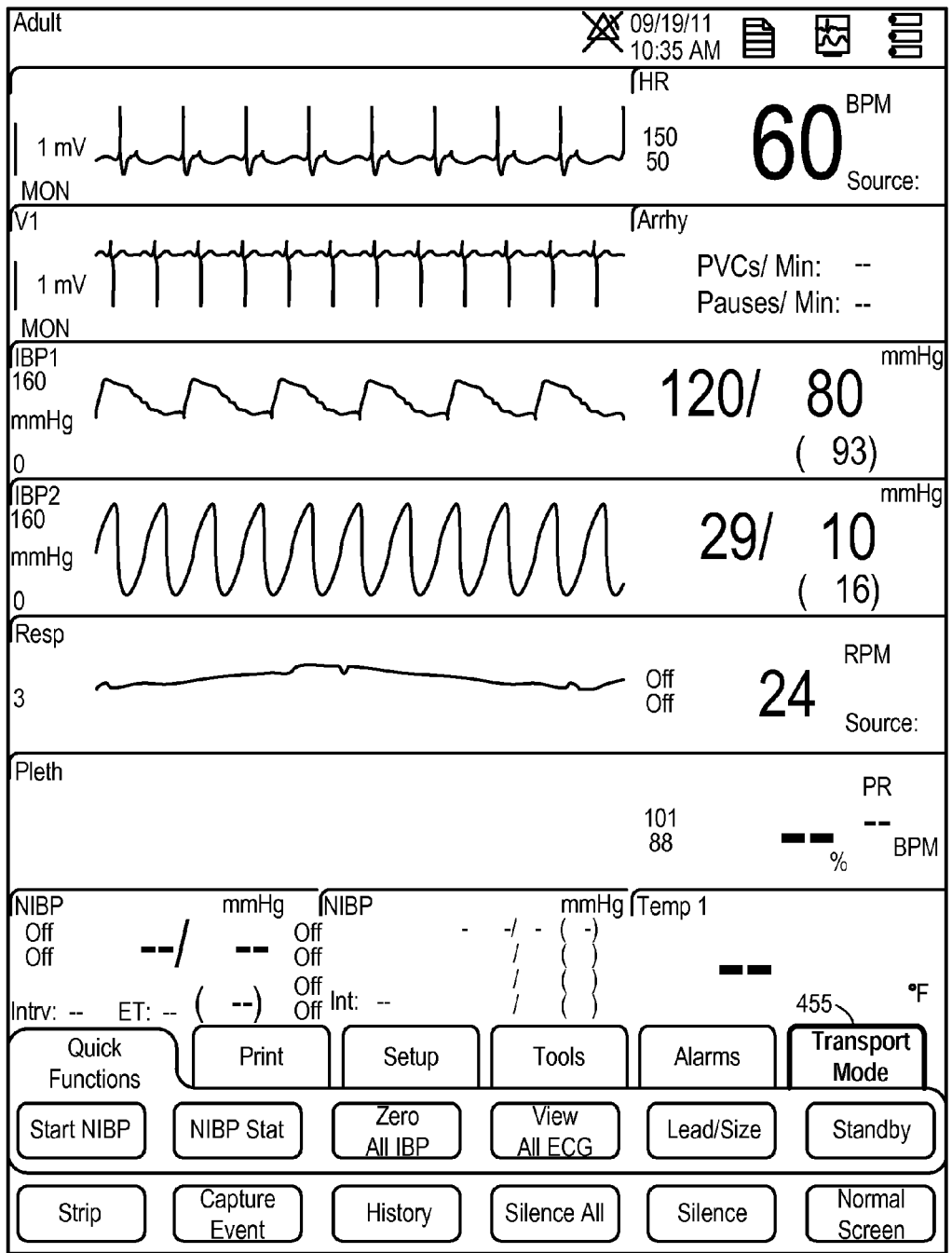
FIG. 4B is an exemplary screenshot of a touch screen display unit of a patient monitoring system in a portrait orientation, including a transport mode menu tab.

FIG. 4B is an exemplary screenshot of a touch screen interface 450 of a display unit of a patient monitoring system in a portrait orientation, including a transport mode icon 455. As illustrated, a transport mode icon 455 within menu tabs 410 may allow an operator to manually cause the display unit to enter a transport mode. According to some embodiments, a transport mode is automatically entered when the display unit is rotated to a landscape orientation based on an orientation input provided by an accelerometer or similar device. Alternatively, an operator must manually provide an input selecting the transport mode. Transport mode may be particularly useful when the patient monitoring system is placed beside a patient in a patient's bed during transport.

A display unit may enter a transport mode by locking the touch screen interface 450, such that the touch screen display does not register touch inputs. Alternatively, the touch screen interface 450 may partially lock, such that the touch screen interface 450 only registers touch inputs that are held for an extended period of time or inputs in a particular area of the screen. For example, the touch screen interface 450 may normally be configured to respond to touch inputs nearly instantaneously, but when placed in transport mode, the touch screen interface 450 may require that touch inputs be held for 2 seconds. Shorter or longer hold times may be required, as may be found useful for a particular application. In addition to locking or partially locking the screen, the display unit may dynamically reconfigure the visual layout of the interface to include information that is particularly relevant to patient transport scenarios. For example, menu tabs 410 may be hidden or removed, waveforms and/or numerical values may be enlarged, and/or less critical information may be removed from the display.

Again, in some embodiments, transport mode is entered into automatically whenever a display unit is placed in a landscape orientation. Alternatively, transport mode may be manually entered in any orientation, or transport mode may be manually entered so long as the display unit is in a landscape orientation. Additionally, once in transport mode, an operator may manually exit the transport mode regardless of the orientation of the display unit. Alternatively, the display unit may automatically exit the transport mode when the orientation is changed, such as for example, from a landscape orientation to a portrait orientation.

Figure 5:
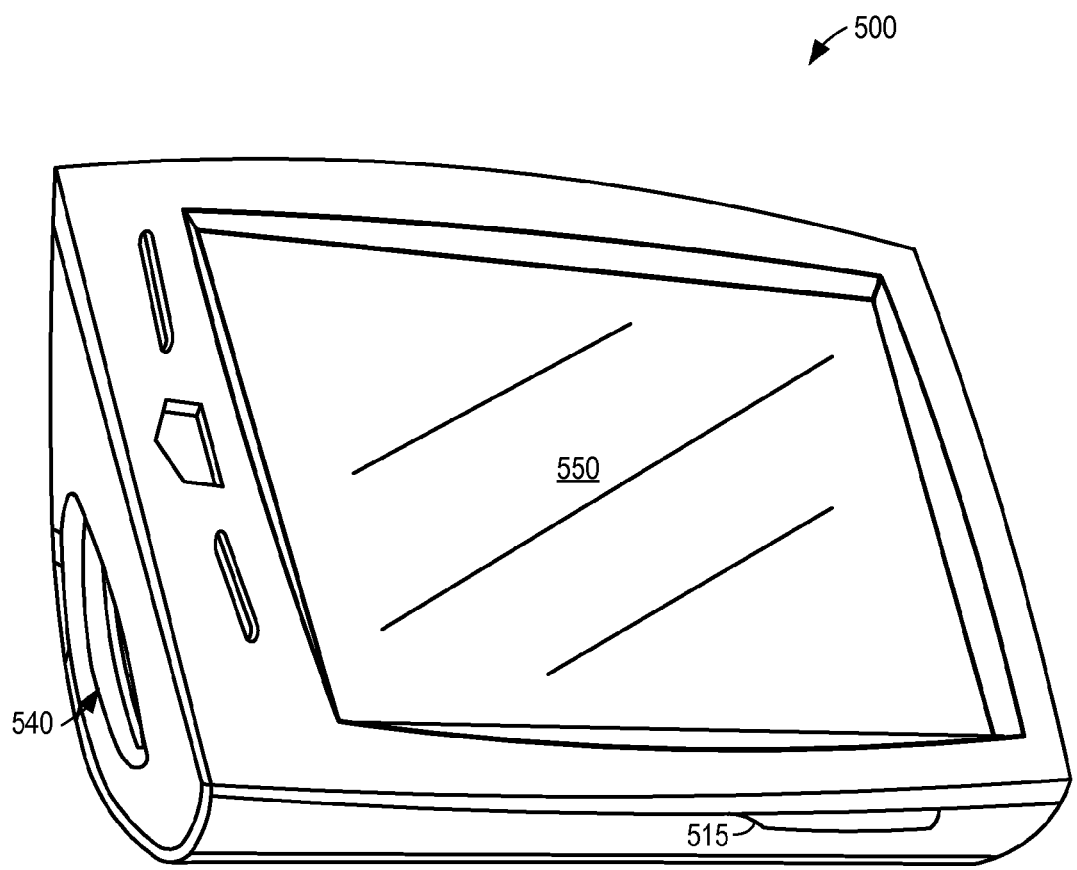
FIG. 5 is a perspective view of a patient monitoring system in a landscape orientation.

FIG. 5 is a perspective view of a patient monitoring system 500 in a landscape orientation. Similar to FIG. 3, a handle 540 may provide a grip for the movement, transportation, and/or rotation of the patient monitoring system 500. Grips 515 on each side of the patient monitoring system 500 may also facilitate the movement, transportation, and/or rotation of the patient monitoring system 500. Additionally, the grips 515 may be used to remove the patient monitoring system 500 from a docking station, a mount, or a stand. For example, the grips 515 may include mechanical or electrical releases that may be actuated by an operator in order to remove the patient monitoring system 500 from a wall mount. Display unit 550 may include an integrated touch screen and be configured to display a visual layout of a touch screen interface, including patient parameter information in the form of various waveforms and/or numerical values.

Figure 6A:
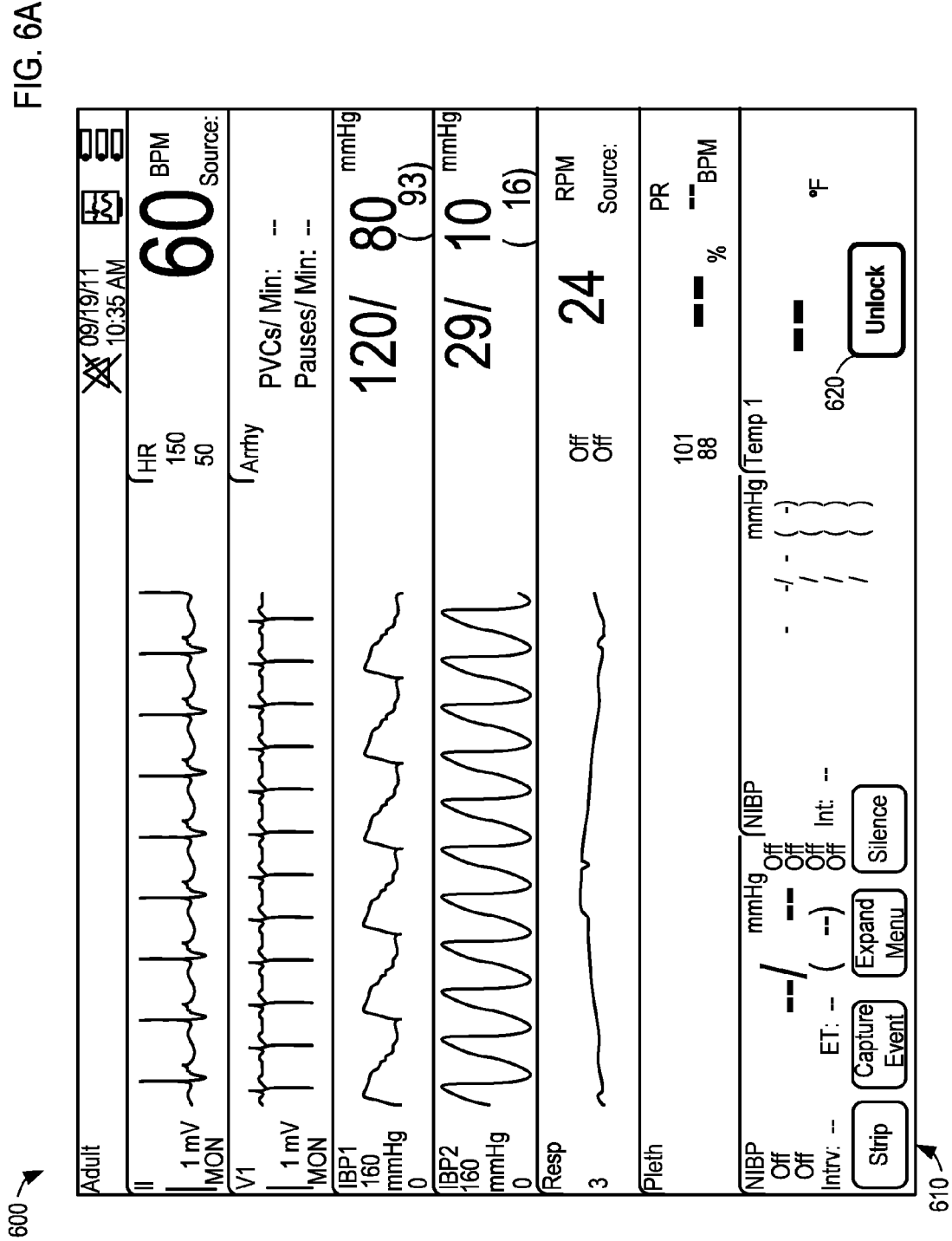
FIG. 6A is an exemplary screenshot of a touch screen display unit of a patient monitoring system in a landscape orientation, including an unlock button.

FIG. 6A is an exemplary screenshot of a touch screen interface 600 of a display unit of a patient monitoring system in a landscape orientation, including an unlock button 620. According to the illustrated embodiment, a display unit has been rotated to a landscape orientation and a visual layout of a touch screen interface 600 has been dynamically reconfigured for display in the landscape orientation. In addition, the touch screen interface 600 has entered a transport mode, either automatically based on an orientation input from an accelerometer or from a user-provided orientation input. As previously described, with the display unit in a transport mode, the touch screen interface 600 may be locked or partially locked.

In a completely locked mode, the menu icons 610, including strip, capture event, expand menu, and silence, may be completely disabled. The unlock icon 620 may be pressed to unlock the menu icons 610. According to various embodiments, the unlock icon 620 requires an extended hold, comprises a physical button or switch on the display unit, and/or requires a double or triple tap in order for the input to register, thus reducing accidental touch inputs during transport. According to another embodiment, the touch screen interface 600 may only be partially locked. According to such an embodiment, the menu icons 610 may be partially locked, such that the touch screen only registers touch inputs that are held for an extended period of time or touch inputs in a limited area of the screen. For example, the touch screen interface 600 may normally be configured to respond to touch inputs nearly instantaneously, but when placed in transport mode the touch screen interface 600 may require touch inputs be held for 2 seconds. Shorter or longer hold times may be required, as may be found useful for a particular application.

Additionally, the visual layout of the touch screen interface 600 may be particularly relevant to patient transport scenarios. For example, the extended menu illustrated in FIGS. 4A and 4B may be removed, hidden, and/or minimized as illustrated in FIG. 6A. Rather than an extended set of menu tabs, only a few menu icons 610 may be visible. An expand menu icon may allow an operator access to an expanded set of menu options.

Figure 6B:
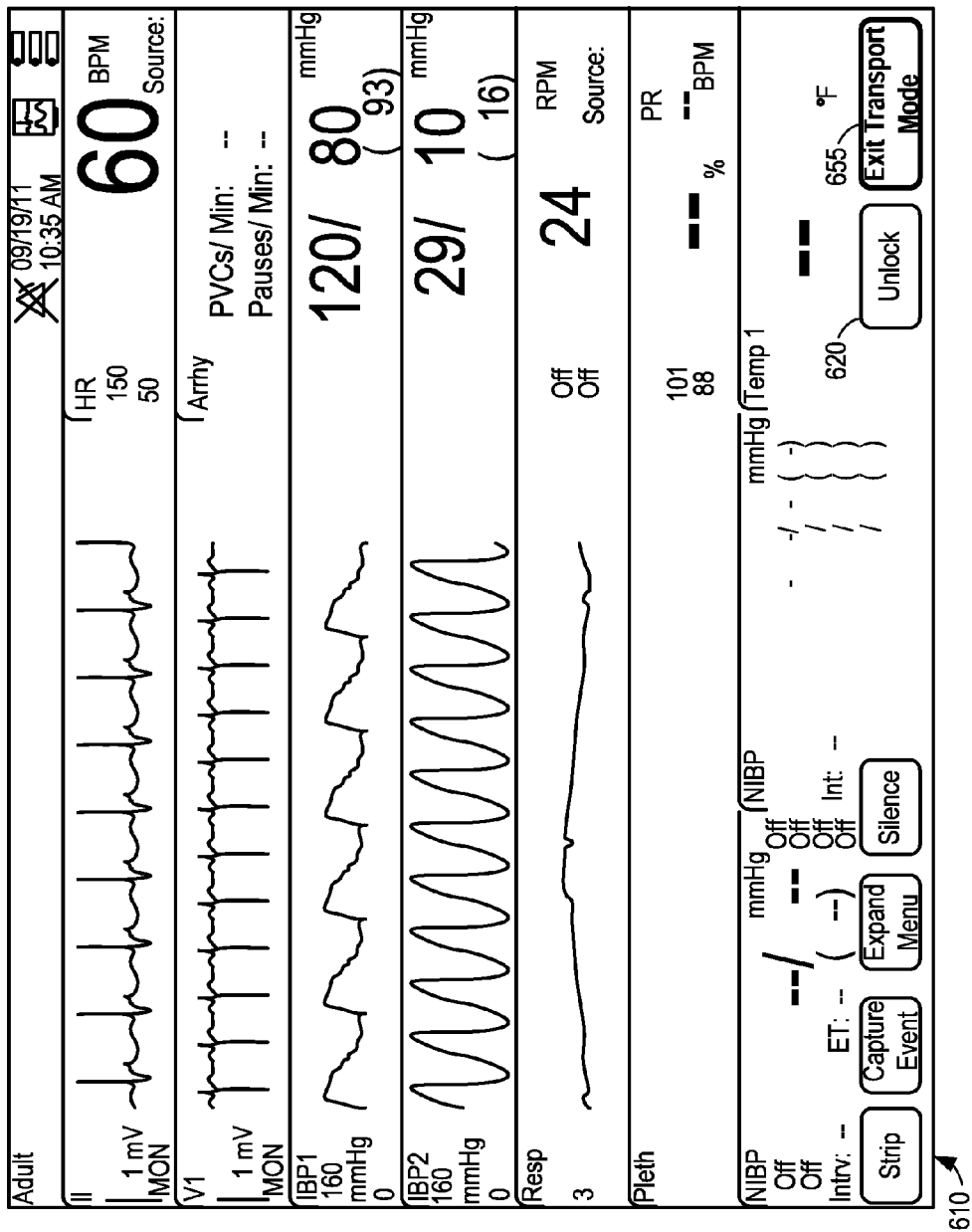
FIG. 6B is an exemplary screenshot of a touch screen display unit of a patient monitoring system in a landscape orientation, including an unlock button and an exit transport mode button.

FIG. 6B is an exemplary screenshot of a touch screen interface 650 of a display unit of a patient monitoring system in a landscape orientation, including an unlock icon 620 and an exit transport mode icon 655. Similar to FIG. 6A, the touch screen interface 650 may have entered a transport mode, either automatically based on an orientation input from an accelerometer or from a manual user-provided orientation input. As previously described, with the display unit in a transport mode, the touch screen interface 650 may be locked or partially locked.

Again, in a completely locked mode, the menu icons 610 may be completely disabled, while in a partially locked mode, the menu icons 610 may require that touch inputs be held for an extended period of time to be registered. In some embodiments, such as in embodiments lacking an accelerometer, the touch screen interface 650 may include an exit transport mode button 655 in order to allow an operator to exit the transport mode when the display unit is rotated to a portrait orientation. According to some embodiments, an orientation icon (not illustrated) is configured to allow an operator to toggle between various orientations, possibly independent of the locked status or transport mode selection.

Accordingly, a patient monitoring system may automatically detect an orientation using an accelerometer and enter a transport mode and/or lock a touch screen interface when placed in a landscape orientation. In other embodiments, locking the screen, selecting an orientation for the visual layout, and/or entering and exiting a transport mode may be manual selections made by an operator via the touch screen interface, a button, a switch, or the like.

Figure 7:
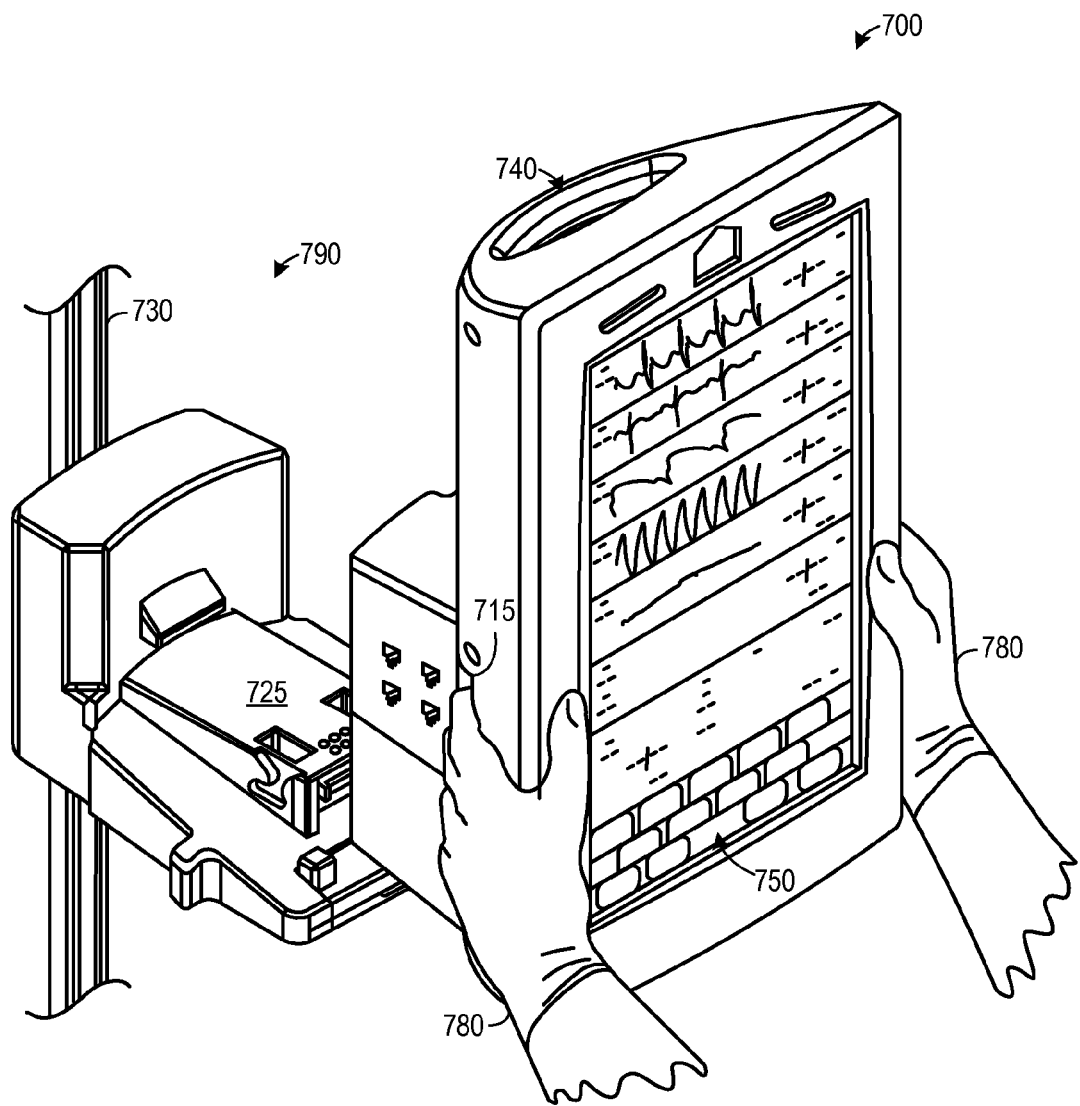
FIG. 7 is a perspective view of a patient monitoring system as it is removed from a wall mount.

FIG. 7 is a perspective view of a patient monitoring system 700 as it is removed from a wall mount 790. As illustrated, the wall mount 790 may include a docking station 725 configured to receive the patient monitoring system 700. The docking station 725 may be secured to the wall with a sliding mount 730, such that the patient monitoring system 700 may be vertically adjusted along the wall. The patient monitoring system 700 may include a handle 740 and grips 715 that may facilitate the remove of the patient monitoring system 700 from the docking station 725.

An operator may use one or both hands 780 to actuate releases located near or behind grips 715. Once the releases have been actuated, the patient monitoring system 700 may be removed from the docking station 725. According to various embodiments, the display unit 750 is configured to continue displaying patient parameter information, including waveform representations and numerical values, while the patient monitoring system 700 is removed from the docking station 725.

Once removed from the docking station 725, the patient monitoring system 700 may be transported or moved to a new location. During transport, the patient monitoring system 700 may continue displaying, recording, and/or uploading patient parameter information. One or more batteries or portable power supplies may be used to power the patient monitoring system 700 during transport.

Figure 8:
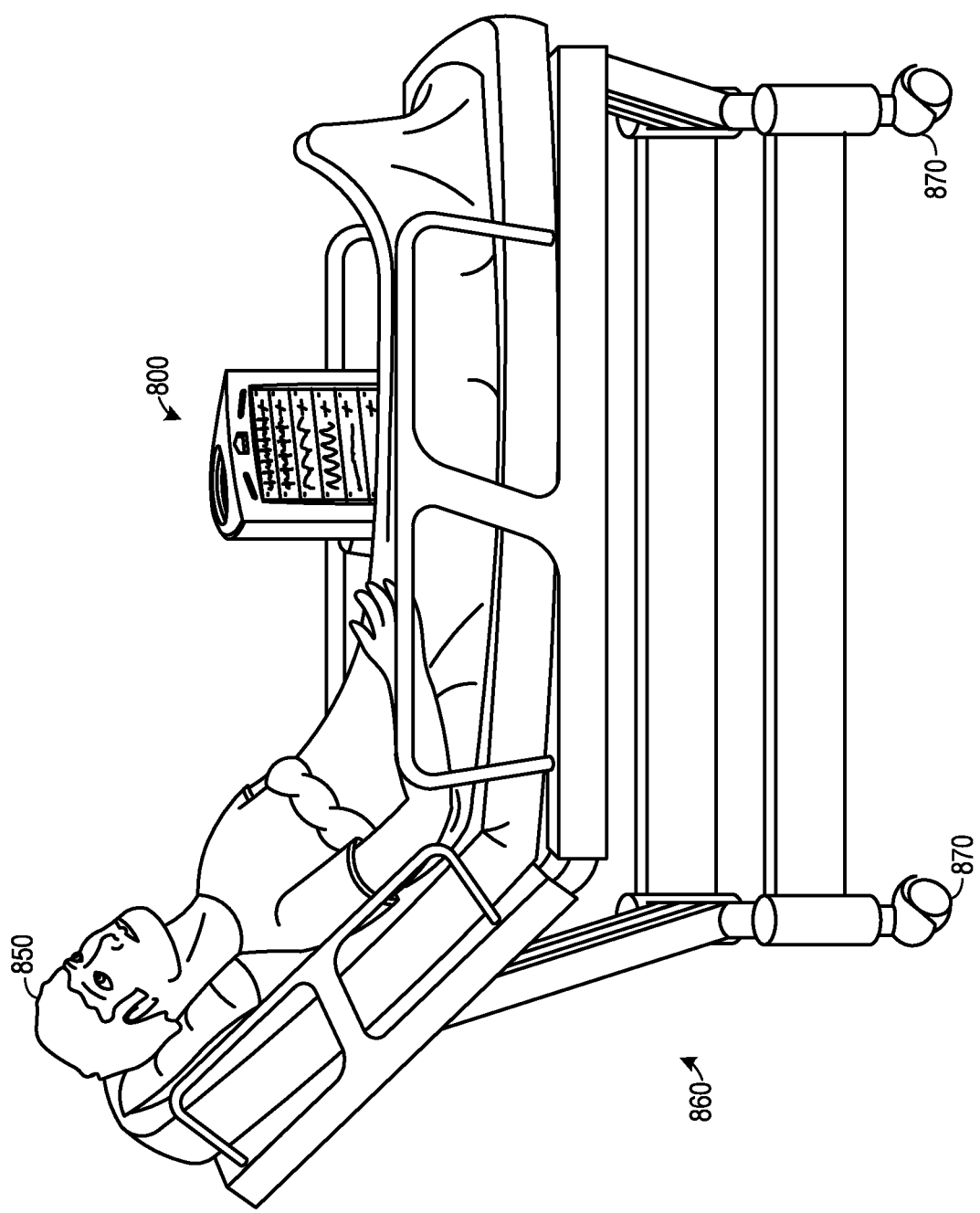
FIG. 8 is a perspective view of a patient monitoring system in a portrait orientation placed beside a patient as the patient is transported.

As illustrated in FIG. 8, a patient monitoring system 800 may be placed beside a patient 850 in a bed 860. According to various embodiments, the bed 860 may be configured with wheels 870 in order to facilitate transportation of the patient 850. The patient monitoring system 800 may be placed in a portrait orientation beside the patient 850 as the patient 850 is transported. According to one embodiment, a medical practitioner or other operator may manually select a transport mode in order to lock or partially lock a touch screen display of the patient monitoring system 800. The transport mode may prevent or reduce accidental touch inputs while the patient monitoring system 800 is transported. Specifically, the patient monitoring system 800 may not register inadvertent touch inputs from the patient 850 or the patient's blankets while the patient monitoring system 800 is in the transport mode.

Figure 9:
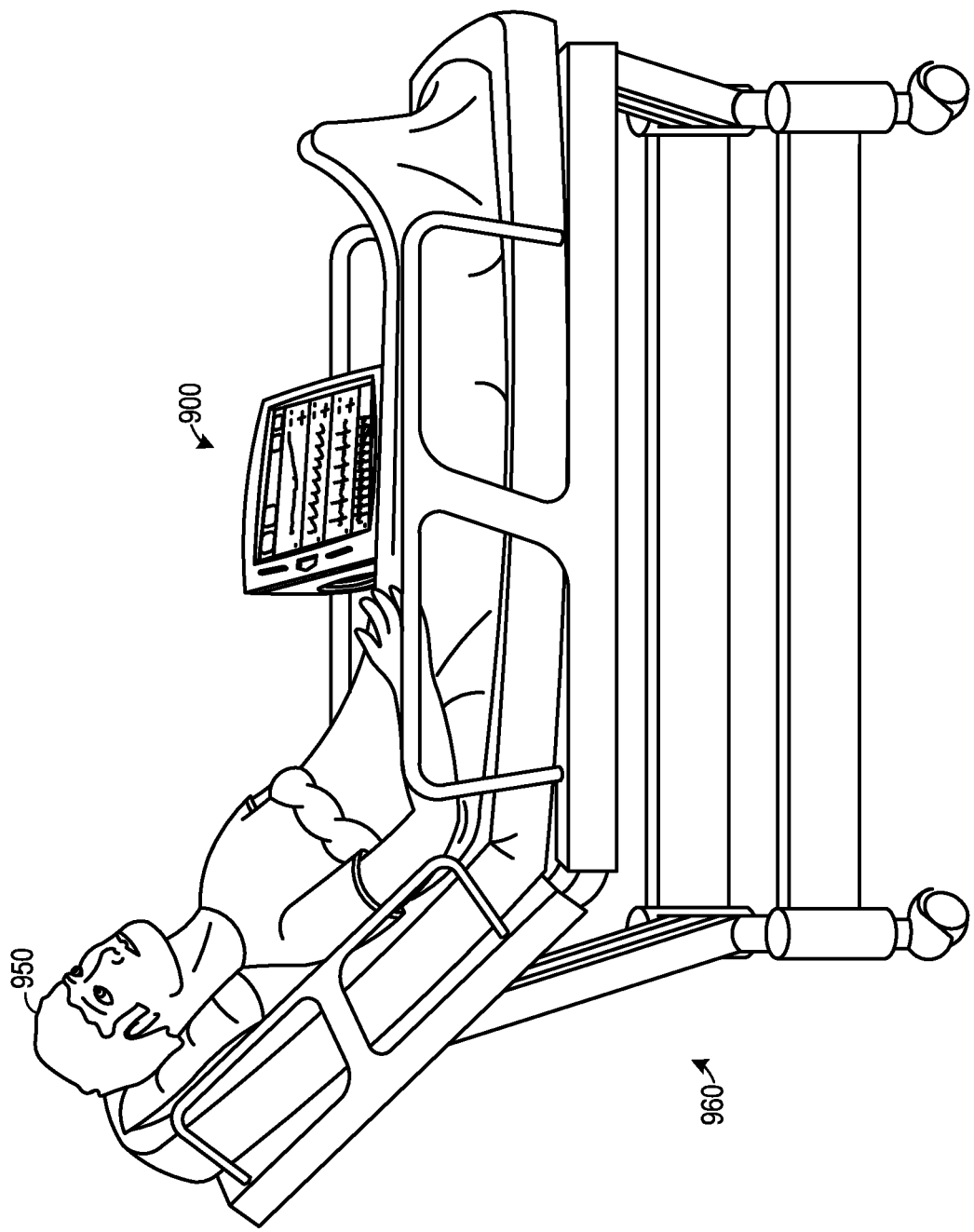
FIG. 9 is a perspective view of a patient monitoring system in a landscape orientation placed beside a patient as the patient is transported.

To increase stability during transport, a patient monitoring system 900 may be rotated to a landscape orientation when placed beside a patient 950 on a bed 960, as illustrated in FIG. 9. According to various embodiments, an accelerometer detects that the patient monitoring system 900 is in the landscape orientation and dynamically reconfigures a visual layout of a touch screen interface for display in the landscape orientation. The visual layout of the touch screen interface may include patient parameter information, such as waveforms and numerical values related to physiological parameters of the patient 950. The patient monitor may be configured to dynamically reconfigure a visual layout of the touch screen interface to include fewer waveforms, larger waveforms, and/or fewer user-selectable menu options when in the landscape orientation than when in the portrait orientation. Additionally, the patient monitoring system 900 may enter a transport mode once it detects that it is in a landscape orientation. The transport mode may include dynamically reconfiguring the visual layout of the touch screen interface to include fewer waveforms, larger waveforms, and/or fewer user-selectable menu options when in the landscape orientation than when in the portrait orientation. Additionally or alternatively, the transport mode may include dynamically reconfiguring the visual layout of the touch screen interface to include patient parameter information specifically relevant to transport scenarios. As previously described, the patient monitoring system 900 may exit the transport mode based on user inputs and/or once it is rotated to a portrait orientation.

In alternative embodiments, the patient monitoring system 900 is not capable of automatically detecting an orientation. Rather, an operator may manually provide an orientation input indicating the orientation of the display unit of the patient monitoring system 900. In such an embodiment, the patient monitoring system 900 may receive the orientation input and then dynamically reconfigure a visual layout of the touch screen interface, including patient parameter information. Additionally, the patient monitoring system 900 may enter the transport mode based on the orientation input or based on additional manual inputs provided by the user.

Figure 10:
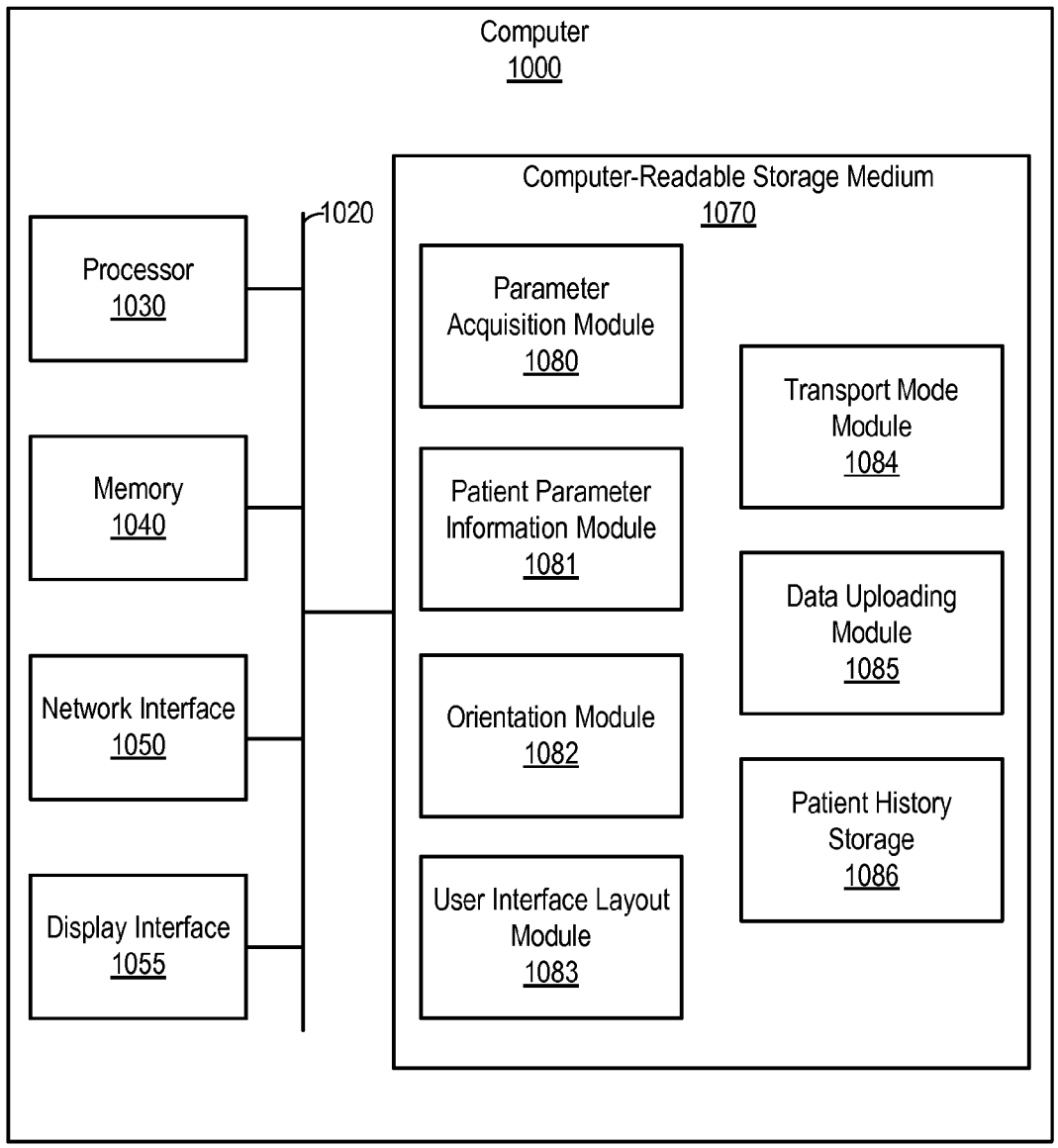
FIG. 10 is a functional block diagram of a computer system that may be used to monitor a patient, reconfigure a user interface layout for landscape and portrait orientations, and allow a display unit to selectively enter a transport mode.

FIG. 10 illustrates a functional block diagram of a computer system 1000 that may be used to monitor a patient and dynamically reconfigure a visual layout of an interface based on an orientation input. As illustrated, a computer 1000 may include a processor 1030, a memory 1040 (RAM), a network interface 1050, a display interface 1055 in communication with a computer-readable storage medium 1070 via a bus 1020. The computer-readable storage medium 1070 may include one or more software modules 1080-1086 configured to generate patient parameter information related to the physiological parameters of a patient and display them on a display unit. The one or more of the software modules 1080-1086 may alternatively be implemented using firmware and/or hardware. Additionally, one or more of the software modules 1080-1086 may be joined together as a single module and/or separated into a plurality of sub-modules. Moreover, the memory 1040, the network interface 1050, and/or the display interface 1055, may be implemented as an external device in communication with the computer system 1000 via a port and/or through a processor 1030.

A parameter acquisition module 1080 may be configured to acquire data signals relating to the physiological parameters of the patient. The patient parameter information module 1081 may be configured to generate patient parameter information relating to the physiological parameters of a patient based on the acquired data signals. The patient parameter information may then be stored in the memory 1040 and/or within the patient history storage 1086. Additionally, a data uploading module 1085 may be used to upload the patient parameter information to a central management system.

An orientation module 1082 may be configured to receive an orientation input corresponding to the orientation of a display unit. For example, the orientation module 1082 may receive an orientation input from an accelerometer indicating whether the display unit is in a portrait orientation or a landscape orientation. As another example, the orientation module 1082 may be configured to receive an orientation input from an accelerometer or tri-axis gyroscope in order to determine a precise orientation, beyond general portrait and landscape orientations. Alternatively or in addition, the orientation module 1082 may be configured to receive an orientation input from an operator indicating whether the display unit is in a portrait orientation or a landscape orientation. Such an embodiment may be particularly useful for patient monitoring systems that do not include an accelerometer or similar device that can automatically detect an orientation of the display unit.

A user interface layout module 1083 may be configured to dynamically reconfigure a visual layout of a user interface for display on the display unit based on the orientation input. The visual layout of the user interface may include, for example, patient parameter information in the form of waveforms and/or numerical values, menu icons, and/or patient identification information. For example, a waveform may graphically illustrate the heart beat of a patient along a timeline and a numerical value may indicate the current heart rate. In one embodiment, the user interface layout module 1083 dynamically reconfigures a visual layout for display in either a portrait layout or a landscape layout based on the received orientation input. The display interface 1055 may then display the visual layout prepared by the user interface layout module 1083.

Additionally, a transport mode module 1084 may be configured to cause the display unit to enter a transport mode based on user input or the orientation input. For example, the transport mode module 1084 may cause the display unit to enter a transport mode when the orientation input received by orientation module 1082 indicates that the display unit is in a landscape orientation. The display unit may automatically exit the transport mode when the orientation is changed from a landscape orientation to a portrait orientation.

The transport mode module 1084 may cause the display unit to enter a transport mode by locking a touch screen interface, such that the touch screen display does not register touch inputs. Alternatively, the touch screen interface may partially lock, such that the touch screen interface only registers touch inputs that are held for an extended period of time or inputs in a particular region of the screen. In addition to locking or partially locking a touch screen, the transport mode module 1084 may communicate with user interface layout module 1083 in order to dynamically reconfigure a visual layout to include information that is particularly relevant to patient transport scenarios. For example, menu tabs may be hidden or removed, waveforms and/or numerical values may be enlarged, and/or less critical information may be removed from the display.

Figure 11:
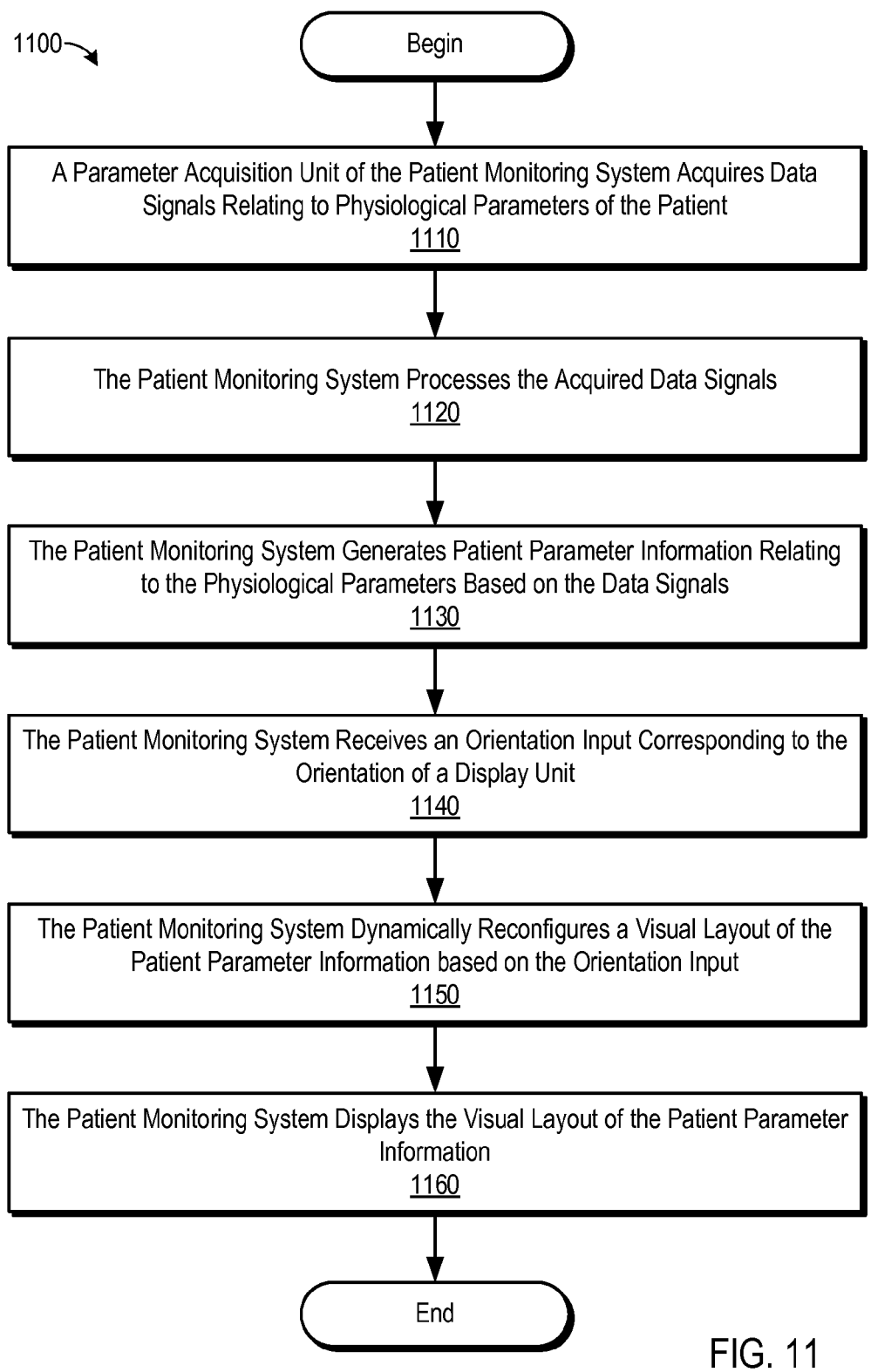
FIG. 11 is a flow chart of an exemplary method for displaying a visual layout of patient parameter information based on the orientation of a display unit.

FIG. 11 is a flow chart of an exemplary method 1100 for displaying a visual layout of a user interface, including patient parameter information, based on the orientation of a display unit. At 1110, a parameter acquisition unit of the patient monitoring system acquires data signals relating to physiological parameters of the patient. For example, the parameter acquisition unit may include various ports configured to receive data signals from physiological sensor probes, such as $SpO_2$ ports.

At 1120, the patient monitoring system processes the acquired data signals, generates patient parameter information relating to the physiological parameters of the patient, at 1130. For example, patient parameter information may be represented by various waveforms and/or numerical values corresponding to the physiological parameters of the patient.

At 1140, the patient monitoring system may receive an orientation input corresponding to the orientation of a display unit. The orientation input may be received from an accelerometer, gyroscopic device, or similar device configured to automatically detect the orientation of the display unit. Alternatively, the orientation input may be received from a user via a manual input, such as via the touch screen interface, a button, or a switch. The patient monitoring system may then dynamically reconfigure a visual layout of the patient parameter information based on the orientation input, at 1150.

For example, a visual layout may be configured for display in either a portrait orientation or a landscape orientation. Additional layouts may be dynamically reconfigured to accommodate additional orientations. Moreover, more than one layout may be possible for a given orientation. In such embodiments, a visual layout for a specific orientation may be based in part on user inputs and in part on orientation inputs automatically provided by an electronic device, such as an accelerometer or gyroscopic device. The patient monitoring system may then display the visual layout of the patient parameter information on the display unit, at 1160. According to various embodiments, the display unit may include a touch screen interface, various buttons or switches, and/or peripheral devices for providing user input.

Figure 12:
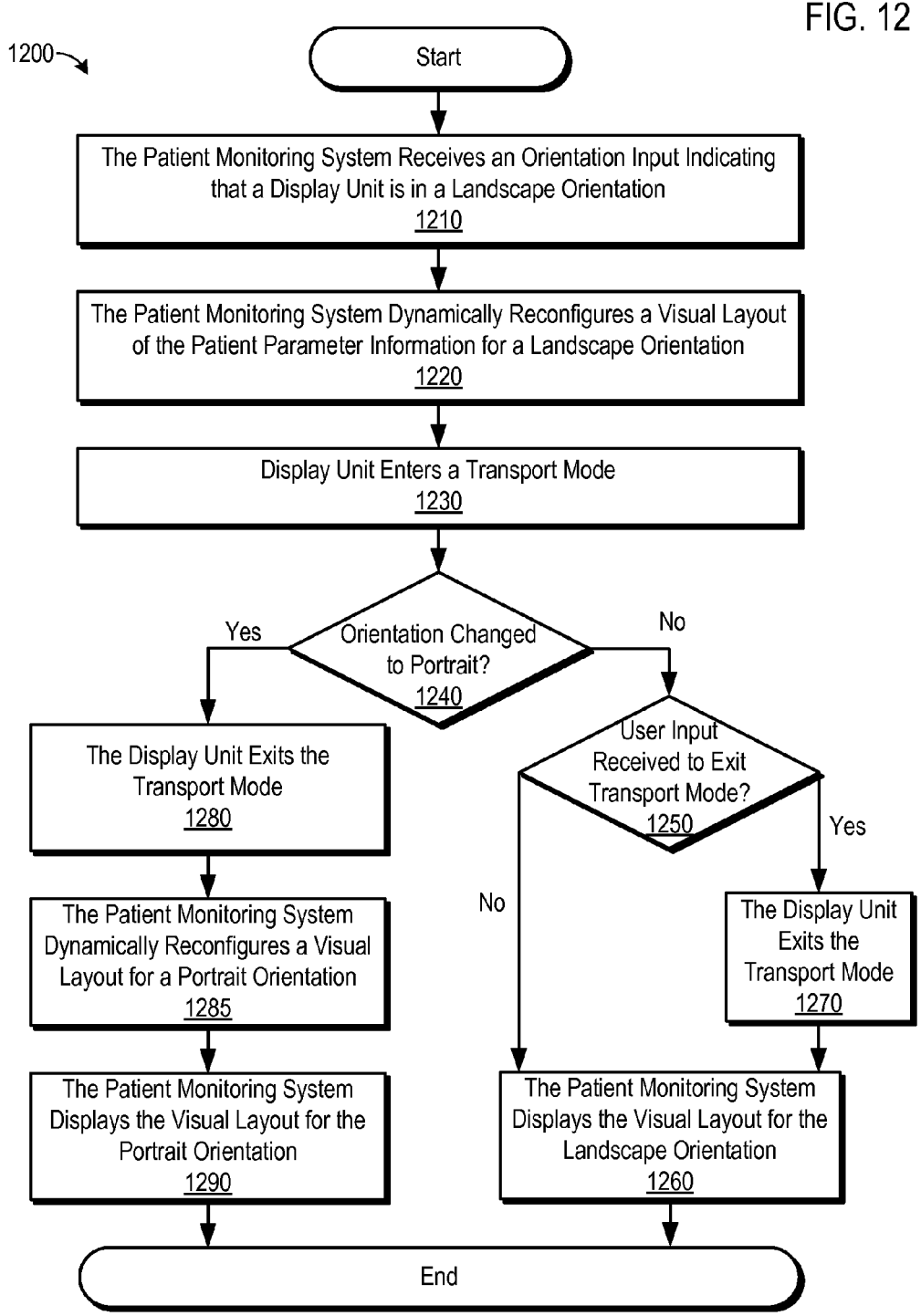
FIG. 12 is a flow chart of an exemplary method for displaying a visual layout of patient parameter information based on the orientation of a display unit and selectively maintaining the display unit in a transport mode.

FIG. 12 is a flow chart of an exemplary method 1200 for displaying a visual layout of a user interface, including patient parameter information, based on the orientation of a display unit and selectively maintaining the display unit in a transport mode. At 1210, the patient monitoring system may receive an orientation input indicating that a display unit is in a landscape orientation. The orientation input may be received from an accelerometer, gyroscopic device, or similar device configured to automatically detect that the display unit is in a landscape orientation. Alternatively, a user may manually provide an input indicating that the display unit is in a landscape orientation. At 1220, the patient monitoring system may then dynamically reconfigure a visual layout of a user interface, including the patient parameter information, for a landscape orientation.

According to various embodiments, when an orientation input indicates that a display unit is in a landscape orientation the display unit may automatically enter a transport mode, at 1230. Alternatively, a user may be required to provide a manual input in order for the display unit to enter a transport mode. The display unit may enter a transport mode by locking or partially locking a touch screen interface, such that the touch screen does not register touch inputs at al or only registers touch inputs that are held for an extended period of time. In addition to locking or partially locking a touch screen, entering a transport mode may include dynamically reconfiguring a visual layout of the display interface and patient parameter information to include information that is particularly relevant to patient transport scenarios. For example, menu tabs may be hidden or removed, waveforms and/or numerical values may be enlarged, and/or less critical information may be removed from the display.

According to some embodiments, if the orientation of the display unit remains in the landscape orientation, at 1240, and a user does not provide an input directing the patient monitoring system to exit the transport mode, at 1250, then the patient monitoring system displays the visual layout for the landscape orientation, at 1260. If the orientation remains in the landscape orientation, at 1240, but the user provides an input directing the patient monitoring system to exit the transport mode, at 1250, then the patient monitoring system may exit the transport mode (e.g., unlock the touch screen interface), at 1270, and continue displaying the visual layout for the landscape orientation, at 1260.

If, however, the orientation is changed to portrait, at 1240, then the display unit exits the transport mode, at 1280. The patient monitoring system may then dynamically reconfigure a visual layout for display in a portrait orientation, at 1285, and display the visual layout for the portrait orientation, at 1290.

This disclosure has been made with reference to various exemplary embodiments including the best mode. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

Additionally, as will be appreciated by one of ordinary skill in the art, principles of the present disclosure may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the invention. The scope of the present invention should, therefore, be determined only by the following claims.

What is claimed is:

1. A method of displaying patient parameter information comprising:
    acquiring, via a parameter acquisition unit of a patient monitoring system, at least one data signal relating to at least one physiological parameter of a patient;
    processing the at least one data signal with a processing unit;
    generating patient parameter information related to the at least one physiological parameter based on the at least one data signal;
    receiving an orientation input corresponding to the orientation of a touch screen display unit of the patient monitoring system; and
    determining that the touch screen display unit is in a landscape orientation and in response to detecting the landscape orientation:
        dynamically reconfiguring a visual layout of at least a portion of the patient parameter information for display on the touch screen display unit of the patient monitoring system in the landscape orientation;
        displaying the visual layout via the touch screen display unit of the patient monitoring system; and
        entering a transport mode in which the visual layout is displayed while a touch input interface of the touch screen display unit is at least partially locked, such that touch inputs are at most received as inputs on a limited basis.

2. The method of claim 1, further comprising receiving a touch input via the touch screen display unit from a user while in the transport mode.

3. The method of claim 1, wherein displaying the visual layout comprises displaying at least a portion of the patient parameter information as a waveform with an associated numerical value.

4. The method of claim 1, wherein the at least one physiological parameter comprises one of a blood pressure, a heart rate, a temperature, a respiration rate, a venous oxygen saturation, and an electrocardiogram.

5. The method of claim 1, wherein receiving an orientation input comprises receiving an input from an accelerometer.

6. The method of claim 1, wherein receiving an orientation input comprises receiving a manual input from an operator.

7. The method of claim 1, wherein receiving an orientation input comprises receiving an input indicating that the display unit is in one of a portrait orientation and a landscape orientation;
    wherein the visual layout of at least a portion of the patient parameter information comprises a plurality of waveforms; and
    wherein when the orientation input indicates that the display unit is in the landscape orientation, the visual layout includes fewer waveforms than when the display input indicates that the display unit is in the portrait orientation.

8. The method of claim 7, wherein
    the visual layout further comprises a plurality of selectable menu icons; and
    wherein when the orientation input indicates that the display unit is in the landscape orientation, the visual layout includes fewer waveforms and fewer selectable menu icons than when the display input indicates that the display unit is in the portrait orientation.

9. The method of claim 1, wherein receiving an orientation input comprises receiving an input indicating that the display unit is in one of a portrait orientation and a landscape orientation.

10. The method of claim 1, wherein entering the transport mode comprises locking the touch screen display, such that the touch screen display does not register touch inputs.

11. The method of claim 1, wherein entering the transport mode comprises partially locking the touch screen display, such that the touch screen display only registers touch inputs that are held for a predetermined time period or touch inputs in a particular area of the touch screen display.

12. The method of claim 1, further comprising the exiting the transport mode when at least one of a first condition and a second condition is satisfied, the first condition comprising the orientation input indicating that the display unit is in the portrait orientation and the second condition comprising receiving a user input to exit the transport mode.

13. A patient monitoring system comprising:
    a parameter acquisition unit configured to acquire at least one data signal relating to at least one physiological parameter of a patient;
    a processing unit in communication with the parameter acquisition unit, the processing unit configured to:
        process the at least one data signal; and generate patient parameter information related to the at least one physiological parameter based on the at least one data signal;

an orientation unit configured to receive an orientation input corresponding to the orientation of a touch screen display unit;

a layout unit in communication with the orientation unit and the processing unit, the layout unit configured to dynamically reconfigure a visual layout of at least a portion of the patient parameter information for display on the touch screen display unit based on the orientation input;

a display interface unit in communication with the layout unit, the display interface unit configured to display the visual layout via the touch screen display unit; and a transport unit configured to cause the touch screen display unit to enter a transport mode when the orientation input indicates that the display unit is in a landscape orientation, wherein in the transport mode a touch input interface of the touch screen display unit is at least partially locked, such that touch inputs are at most received on a limited basis while the visual layout is displayed.

14. The patient monitoring system of claim 13, wherein the dynamically reconfigured layout comprises at least a portion of the patient parameter information represented as a waveform with an associated numerical value.

15. The patient monitoring system of claim 13, wherein the at least one physiological parameter comprises one of a blood pressure, a heart rate, a temperature, a respiration rate, a venous oxygen saturation, and an electrocardiogram.

16. The patient monitoring system of claim 13, wherein the orientation unit is configured to receive an orientation input an accelerometer.

17. The patient monitoring system of claim 13 wherein the orientation unit is configured to receive a manual orientation input from an operator.

18. The patient monitoring system of claim 13, wherein the orientation unit is configured to receive an orientation input indicating that the display unit is in one of a portrait orientation and a landscape orientation;

wherein the visual layout of at least a portion of the patient parameter information comprises a plurality of waveforms; and wherein when the orientation input indicates that the display unit is in the landscape orientation, the visual layout includes fewer waveforms than when the display input indicates that the display unit is in the portrait orientation.

19. The patient monitoring system of claim 13, wherein the display unit comprises a touch screen display;

the visual layout of at least a portion of the patient parameter information comprises a plurality of selectable menu icons; and wherein when the orientation input indicates that the display unit is in the landscape orientation, the visual layout includes fewer selectable menu icons than when the display input indicates that the display unit is in the portrait orientation.

20. The patient monitoring system of claim 13, wherein the orientation unit is configured to receive an orientation input indicating that the display unit is in one of a portrait orientation and a landscape orientation.

21. The patient monitoring system of claim 13, wherein in the transport mode, the transport unit is configured to lock the touch screen display, such that the touch screen display does not register touch inputs.

22. The patient monitoring system of claim 13, herein in the transport mode, the transport unit is configured to partially lock the touch screen display, such that the touch screen display only registers touch inputs that are held for a predetermined time period.

23. The patient monitoring system of claim 13, wherein the transport unit is configured to cause the transport unit to exit the transport mode when at least one of a first condition and a second condition is satisfied, the first condition comprising the orientation unit receiving an orientation input indicating that the display unit is in the portrait orientation and the second condition comprising receiving a user input to exit the transport mode.

24. A non-transitory computer-readable storage medium storing instructions that, when executed by a processor, are configured to cause the processor to perform a method, the method comprising:

acquiring at least one data signal relating to at least one physiological parameter of a patient;

processing the at least one data signal;

generating patient parameter information related to the at least one physiological parameter based on the at least one data signal;

receiving an orientation input corresponding to the orientation of a touch screen display unit; and determining that the touch screen display unit is in a landscape orientation an in response to detecting the landscape orientation:

dynamically reconfiguring a visual layout of at least a portion of the patent parameter information for display on the touch screen display unit; and entering a transport mode in which the visual layout is configured to be displayed while a touch input interface of the touch screen display unit is configured to be at least partially locked, such that touch inputs are at most received as inputs on a limited basis.

25. The non-transitory computer-readable storage medium of claim 24, wherein displaying the visual layout comprises displaying at least a portion of the patient parameter information as a waveform with an associated numerical value.

26. The non-transitory computer-readable storage medium of claim 24, wherein the at least one physiological parameter comprises one of a blood pressure, a heart rate, a temperature, a respiration rate, a venous oxygen saturation, and an electrocardiogram.

27. The non-transitory computer-readable storage medium of claim 24, wherein receiving an orientation input comprises receiving an input from an accelerometer.

28. The non-transitory computer-readable storage medium of claim 24, wherein receiving an orientation input comprises receiving a manual input from an operator.

29. The non-transitory computer-readable storage medium of claim 24, wherein receiving an orientation input comprises receiving an input indicating that the display unit is in one of a portrait orientation and a landscape orientation;

wherein the visual layout of at least a portion of the patient parameter information comprises a plurality of waveforms; and wherein when the orientation input indicates that the display unit is in the landscape orientation, the visual layout includes fewer waveforms than when the display input indicates that the display unit is in the portrait orientation.

30. The non-transitory computer-readable storage medium of claim 24, wherein receiving an orientation input comprises receiving an input indicating that the display unit is in one of a portrait orientation and a landscape orientation;

wherein the display unit comprises a touch screen display;

wherein the visual layout of at least a portion of the patient parameter information comprises a plurality of selectable menu icons; and wherein when the orientation input indicates that the display unit is in the landscape orientation, the visual layout includes fewer selectable menu icons than when the display input indicates that the display unit is in the portrait orientation.

31. The non-transitory computer-readable storage medium of claim 24, wherein receiving an orientation input comprises receiving an input indicating that the display unit is in one of a portrait orientation and a landscape orientation.

32. The non-transitory computer-readable storage medium of claim 24, wherein entering the transport mode comprises locking the touch screen display, such that the touch screen display does not register touch inputs.

33. The non-transitory computer-readable storage medium of claim 24, wherein entering the transport mode comprises partially locking the touch screen display, such that the touch screen display only registers touch inputs that are held for a predetermined time period.

34. The non-transitory computer-readable storage medium of claim 24, further comprising the touch screen display exiting the transport mode when at least one of a first condition and a second condition is satisfied, the first condition comprising the orientation input indicating that the display unit is in the portrait orientation and the second condition comprising receiving a user input to exit the transport mode.

\* \* \* \* \*